United States Patent [19]  
Knappwost

[11] Patent Number: 4,847,086  
[45] Date of Patent: Jul. 11, 1989

[54] AGENT FOR INCREASING THE PH VALUE OF DENTAL PLAQUE AND PROCESS FOR ITS PREPARATION

[75] Inventor: Adolf Knappwost, Alfeld, Fed. Rep. of Germany

[73] Assignee: Neutralith Antikaries GmbH & Co. KG, Fed. Rep. of Germany

[21] Appl. No.: 149,897

[22] Filed: Jan. 28, 1988

Related U.S. Application Data

[63] Continuation of Ser. No. 834,327, Jan. 9, 1986, abandoned.

[30] Foreign Application Priority Data

May 10, 1984 [DE] Fed. Rep. of Germany ....... 3417393

[51] Int. Cl.⁴ ................. A01N 59/06; A61K 7/16; A23G 3/30; C01F 5/24
[52] U.S. Cl. ................. 424/687; 423/430; 106/464; 424/49; 426/3; 426/74; 426/549; 426/660
[58] Field of Search .......... 423/430, 431, 432; 424/156, 49; 106/464, 306

[56] References Cited

U.S. PATENT DOCUMENTS

| 3,940,550 | 2/1976 | Delfosse et al. ............... 106/214 |
| 4,237,147 | 12/1980 | Merten et al. ............... 423/430 |
| 4,244,933 | 1/1981 | Shibazaki et al. ............... 423/430 |
| 4,257,817 | 3/1981 | Mathur et al. ............... 423/430 |
| 4,279,661 | 7/1981 | Strauch et al. ............... 423/430 |
| 4,446,135 | 5/1984 | Fountaine ............... 424/156 |
| 4,656,028 | 4/1987 | Cuca ............... 424/156 |
| 4,678,662 | 7/1987 | Chan ............... 106/306 |

FOREIGN PATENT DOCUMENTS

| 53-14198 | 2/1978 | Japan ............... 423/430 |
| 59-64527 | 4/1984 | Japan ............... 423/430 |
| 60-231744 | 11/1985 | Japan ............... 423/431 |
| 604822 | 4/1978 | U.S.S.R. ............... 423/430 |
| 604823 | 4/1978 | U.S.S.R. ............... 423/430 |
| 962812 | 7/1964 | United Kingdom ............... 423/432 |

Primary Examiner—Gary P. Straub  
Attorney, Agent, or Firm—Wegner & Bretschneider

[57] ABSTRACT

An agent for increasing the pH value of dental plaque, which contains at least one highly disperse, poorly soluble oxide, hydroxide or pure salt of one or more alkaline earth metal elements and a weak acid, having a specific surface area greater than 6 m²/g and a concentration of lattice defects which corresponds to a half width of the X-ray peaks for Cu-Kα radiation at glancing angles from 20° to 23° of more than 0.25 degrees, and a process for its preparation.

10 Claims, No Drawings

AGENT FOR INCREASING THE PH VALUE OF DENTAL PLAQUE AND PROCESS FOR ITS PREPARATION

This application is a file wrapper continuation of U.S. application Ser. No. 834,327, filed Jan. 9, 1986, now abandoned.

DESCRIPTION

The invention relates to an agent for increasing the pH value of dental plaque, and a process for its preparation.

It is known that caries are caused by dissolution of the hard mineral tooth substance hydroxylapatite [$Ca_{10}(PO_4)_6(OH)_2$] by organic acids (lactic acid, acetic acid, formic acid, etc.) which are formed as metabolic products in the enzymatic conversion of dissolved carbohydrates, such as sucrose, glucose, etc., by acidogenic bacteria in the dental plaque. After the consumption of, for example, sucrose or glucose or of starch which can be decomposed in the saliva, the formation of these acids begins in the course of a few minutes, so that the pH value in the dental plaque falls to values of 5, and frequently even lower, in the course of about 20 to 30 minutes. However, as the pH value decreases, the solubility of the hydroxylapatite in water increases sharply. At 37° C., our own measurements show that it is 12.5 mg/l at a pH value of 7.0 and reaches a value of 628 mg/l at a pH value of 5.0. At these low pH values, the high solubility cannot be compensated by remineralization by the calcium, phosphate and hydroxyl ions present in the saliva, since the hydroxyl ion concentration, like the phosphate concentration, is several powers of ten lower than the values required in order to exceed the solubility product of the hydroxylapatite.

In the interaction between the rate of dissolution $V_L$ and the rate of remineralisation $V_{Rem}$ of hydroxylapatite, the former predominates, so that the condition $V_L > V_{Rem}$, which according to the remineralization theory of caries implies progressive caries, is satisfied.

On the other hand, it is known that remineralization of hard tooth substance underneath the dental plaque can be forced by a relatively high concentration of fluoride ions ($\geq 10^{-3}$ mole/l) in the saliva, since the fluoride ions are capable of replacing the hydroxyl ions in the apatite. However, a large number of difficulties are encountered with regard to the peroral uptake of fluoride doses which produce such a fluoride concentration in the saliva.

It is the object of the present invention to provide an agent which allows the pH in the dental plaque to fall only slightly if at all, or even to increase slightly, after the consumption of fermentable carbohydrates, so that the rate of dissolution $V_L$ is drastically reduced and remineralization of the tooth enamel is effected in this manner.

It would of course be possible to add a few per cent of an acid-binding substance to the foodstuffs or consumables in question. However, dissolved alkaline substances, for example salts, cannot be employed for this purpose, owing to their unpleasant taste. The only suitable substances, therefore, are poorly soluble substances which dissolve rapidly in the acids. However, experiments with commercial precipitated calcium carbonate did not give a satisfactory effect when the change in the pH value in the dental plaque was monitored with the aid of a pH-sensitive microelectrode; apart from this, disadvantages in terms of taste were also found.

It is also known that the specific surface area of precipitated neutralizing powder has to be greater than 6 $m^2/g$ if such a powder is to penetrate into the dental plaque in sufficient amounts as a result of the flow during chewing. For physicochemical reasons (Kelvin equation), such a high specific surface area cannot be achieved by conversion of suspended calcium hydroxide to the carbonate. However, by abruptly combining relatively highly concentrated solutions of calcium nitrate and ammonium carbonate in the presence of a surfactant and of protective colloids as crystal growth inhibitors, it was possible to obtain calcium carbonate having a specific surface area greater than 10 $m^2/g$ by precipitation. When this highly disperse calcium carbonate is added, in an amount of about 1% by weight, to the cariogenic substances (icing sugar, cakes, bread), there is scarcely any reduction in the pH value of the dental plaque compared with the undoped material. Moreover, the preparation of relatively large amounts of the highly disperse calcium carbonate formed by this or a similar precipitation method is difficult and uneconomical owing to the filtration required and the necessity of substantially freeing the precipitated material from the salts formed during the preparation and from the surfactant by repeated washing.

It has been found, surprisingly, that highly disperse, poorly soluble salts of one or more alkaline earth metal elements and a weak acid, having a particular specific surface area and a particular concentration of lattice defects, have a surprisingly pronounced effect on the reduction of the pH value of the dental plaque.

The object discussed above is therefore achieved by means of the agent according to the principal claim.

The invention therefore relates to an agent for increasing the pH value of the dental plaque or the dental deposits, which agent contains at least one highly disperse, poorly soluble oxide, hydroxide or pure salt of one or more alkaline earth metal elements and a weak acid, having a specific surface area greater than 6 $m^2/g$ and a concentration of lattice defects which corresponds to a half width of the X-ray peaks for Cu-K$\alpha$ radiation at glancing angles from 20 to 23° of more than 0.25 degrees.

The alkaline earth metal compounds present in the agent according to the invention preferably possess a specific surface area greater than 10 $m^2/g$ and a concentration of lattice defects which corresponds to a half width of the X-ray peaks for Cu-K$\alpha$ radiation at glancing angles from 20° to 23° of more than 0.30 degrees.

A specific surface area of the $CaCO_3$ of 10 $m^2/g$ corresponds to a mean particle size (equivalent cube edge) of $a = 0.22$ μm. The relationship between this particle size a and the specific surface area $0_{spec}$ is given by $a = 6/0_{spec} \cdot \rho$, where $\rho$ represents the density of the material.

According to the invention, all physiologically acceptable alkaline earth metal salts of acids which, with lactic acid, form a buffer system whose pH value is greater than 5.7 can be used as alkaline earth metal compounds. Hence, the alkaline earth metal phosphates already suggested, which with lactic acid form a buffer system whose pH value is about 4.5, cannot be employed. The agent of the invention therefore preferably contains, as the alkaline earth metal compound, carbonates, silicates, lactates, tartrates, aluminates and/or in particular hydroxides and oxides of calcium and/or magnesium which have been aged by high-temperature treatment, or double salts based on these compounds The agent according to the invention can contain the highly disperse alkaline earth metal compounds as the sole component or may furthermore contain other conventional binders, carriers, auxiliaries and/or extenders which do not exhibit any cariogenic action and are permitted under the food law. When used according to regulations, the agent according to the invention is preferably added to the foodstuffs or consumables, for example to the sugar or other hydrocarbons used in the preparation of such products, or to bakers' produce and in particular confectionery and candy, such as boiled sweets, soft sweets, chocolate and the like. In the case of foodstuffs or consumables which are consumed predominantly by sucking, care must be taken to ensure that the particle size of the alkaline earth metal salts is sufficiently small in order to avoid having an adverse effect on the organoleptic properties of the product treated with the agent according to the invention.

The highly disperse alkaline earth metal compounds present in the agent according to the invention, for example calcium carbonate, magnesium carbonate or double salts of these alkaline earth metal carbonates, can be prepared by wet-milling of the natural materials in a nonaqueous liquid, in order to avoid an increase in particle size due to so-called Ostwald maturing during the separation and drying processes. The products obtained in this procedure have specific surface areas of about 15 $m^2/g$ and display a good action with regard to the reduction in the pH value of the dental plaque.

The specific surface area of the highly disperse alkaline earth metal salts which has been discussed above is determined by the BET method.

It has been found that the rate of the reaction of the highly disperse powders with the acids present in the dental plaque not only depends on the specific surface area of the powders but also increases with the concentration of the various lattice defects, and it has therefor proven advantageous to achieve a relatively high concentration of lattice defects. It has been found that this can be achieved by subjecting the mill base to greater shock by dry-milling. The concentration of lattice defects achieved is then reflected in a broadening of the X-ray peaks. Such a broadening is also observed with decreasing particle size. However, the effects, on the broadening of the X-ray peaks, due to the particle size on the one hand and the concentration of lattice defects on the other hand can be readily differentiated from one another since particularly the effect of the lattice defects in this particle size range (0.1 $\mu$m) is substantially greater than that based on the particle size of a specific surface area. The lattice defect effect is quantified on the basis that it is completely eliminated by heating the compounds in a closed tube at 750° C. for 2 hours.

The invention therefore also relates to a process for the preparation of the highly disperse alkaline earth metal compounds present in the agent according to the invention, wherein the alkaline earth metal compounds are dry-milled until a concentration of lattice defects which corresponds to a half width of the X-ray peaks for Cu-K$\alpha$ radiation at glancing angles from 20 to 23° of more than 0.25 degrees is reached. During this milling procedure, the specific surface area of more than 6 $m^2/g$, which is an essential feature of the invention, is also established. For example, dry-milling calcium carbonate (calcite) in a ball mill or vibratory mill for 120 minutes directly gives a specific surface area of 9 $m^2/g$ and a half width of the X-ray peaks under the stated conditions of about 0.40 degrees. Regarding their pH-increasing action on the dental plaque, the products obtained in this manner correspond to the wet-milled products having a specific surface area of 16 $m^2/g$, which have a substantially greater concentration of lattice defects.

It has also been found, surprisingly, that a specific surface area about 30% greater can be achieved under otherwise identical milling conditions if the dry-milling is carried out in air or nitrogen, the vapours of pure polar liquids having a boiling point below 130° C., such as water or organic liquids, being added to these gases.

The invention therefore also relates to a particularly preferred embodiment of the process discussed, wherein the dry-milling is carried out in an atmosphere which, in addition to air or nitrogen, contains the vapors of pure polar liquids having a boiling point below 130° C., preferably below 105° C., or of mixtures of such polar liquids. Water or organic liquids, such as low molecular weight alcohols having, preferably, 1 to 5 carbon atoms, in particular methanol, ethanol or the like, or ketones or more highly polarisable liquids, are preferably used as such polar liquids.

The products obtained in this manner have proven the most suitable ones in respect of their action in increasing the pH. Furthermore, they show no tendency to cake during the milling process and during addition to the cariogenic foodstuffs and consumables.

A pure alkaline earth metal compound obtained by precipitation and/or premilled is advantageously used as the starting material in the process according to the invention.

The example which follows serves to illustrate the invention further.

EXAMPLE

A vibratory mill having a capacity of 15 l is charged with 6 kg of a premilled calcite having a specific surface area of 3 $m^2/g$, and is flushed with nitrogen. Thereafter, the mill is closed, and 35 g of ethanol are added via a sluice. After milling has been carried out for 120 minutes, the finished mill base is removed from the mill and dried in a stream of air at a temperature of about 60° C. A highly disperse calcite powder is obtained which has a specific surface area of 12 $m^2/g$ and a concentration of lattice defects which corresponds to a half width of the X-ray peaks for Cu-K$\alpha$ radiation at angles from 20 to 23° of 0.45 degrees.

I claim:
1. A method for increasing the pH value of dental plaque, comprising:
   orally contacting the dental plaque with at least one crystalline compound selected from calcium carbonate, calcium lactate and calcium tartrate for a time sufficient to increase the pH, said compound having a specific surface area greater than 6 $m^2/g$ and exhibiting reversible crystal lattice defects in a concentration corresponding to the broadening of the half-width of the X-ray peak for Cu-K radiation at glancing angles of from 20° to 23° of more than 0.25 degrees compared to the half-width of the same material free of such lattice defects.

2. The method according to claim 1, wherein said compound has a specific surface area greater than 10 $m^2/g$.

3. The method according to claim 1, wherein said compound has a concentration of lattice defects corresponding to said half-width of the X-ray peaks for Cu-K radiation at glancing angles of from 20° to 23° of more than 0.30 degrees.

4. The method according to claim 1, wherein said compound is administered in combination with a conventional binder, carrier, auxiliary, or extender.

5. The method according to claim 1, wherein said compound is used in combination with baked goods, confectionery, candy, boiled sweets, soft sweets or chocolate.

6. The method according to claim 1, wherein said compound is calcite.

7. A method for increasing the pH value of dental plaque, comprising:
orally contacting the dental plaque with at least one crystalline compound selected from calcium carbonate, calcium lactate and calcium tartrate for a time sufficient to increase the pH, said compound having a specific surface area greater than 6 m$^2$/g, wherein said crystalline compound is obtained by dry-milling in an atmosphere containing air or nitrogen and the vapors of pure organic polar liquids having a boiling point below 130° C., or mixtures of said polar organic liquids, until a concentration of reversible lattice defects corresponding to the broadening of the half-width of the X-ray peaks for Cu-K radiation at glancing angles of from 20° to 23° of more than 0.25 degrees, compared to the half-width of the same compound free of such lattice defects, is reached.

8. The method according to claim 4, wherein said organic polar liquid is an alcohol.

9. The method according to claim 4, wherein said organic polar liquid is a ketone.

10. The method according to claim 4, wherein said organic polar liquid is ethanol.

* * * * *